(12) United States Patent
Leibowitz et al.

(10) Patent No.: US 8,252,013 B2
(45) Date of Patent: Aug. 28, 2012

(54) EXPANDABLE SURGICAL ACCESS DEVICE AND METHODS OF USE

(75) Inventors: Carla Leibowitz, San Carlos, CA (US); Gary A. Schneiderman, Sacramento, CA (US)

(73) Assignee: Kyphon Sarl, Neuchatel (CH)

( * ) Notice: Subject to any disclaimer, the term of this patent is extended or adjusted under 35 U.S.C. 154(b) by 400 days.

(21) Appl. No.: 12/112,781

(22) Filed: Apr. 30, 2008

(65) Prior Publication Data
US 2009/0275890 A1 Nov. 5, 2009

(51) Int. Cl.
*A61M 29/02* (2006.01)
(52) U.S. Cl. ........ 606/192
(58) Field of Classification Search ........ 600/184, 600/201, 206–208; 606/57, 90, 105, 119, 606/191–197
See application file for complete search history.

(56) References Cited

U.S. PATENT DOCUMENTS

| | | | |
|---|---|---|---|
| 4,670,313 A | 6/1987 | Saudagar | |
| 4,932,959 A * | 6/1990 | Horzewski et al. | 606/194 |
| 5,868,753 A * | 2/1999 | Schatz | 606/108 |
| 6,010,531 A | 1/2000 | Donlon et al. | |
| 6,171,299 B1 * | 1/2001 | Bonutti | 606/1 |
| 6,231,544 B1 | 5/2001 | Tsugita et al. | |
| 6,235,043 B1 | 5/2001 | Reiley et al. | |
| 6,592,546 B1 | 7/2003 | Barbut et al. | |
| 7,144,386 B2 | 12/2006 | Korkor et al. | |
| 7,179,225 B2 | 2/2007 | Shluzas et al. | |
| 2003/0014076 A1 * | 1/2003 | Mollenauer et al. | 606/213 |
| 2003/0181939 A1 | 9/2003 | Bonutti | |
| 2006/0217755 A1 | 9/2006 | Eversull et al. | |
| 2007/0299455 A1 | 12/2007 | Stevens et al. | |

FOREIGN PATENT DOCUMENTS
WO WO 2008/021018 A1 2/2008

OTHER PUBLICATIONS
International Search Report for US Application US2009/042128 mailed on Oct. 19, 2009.

* cited by examiner

*Primary Examiner* — Ryan Severson

(57) ABSTRACT

An expandable surgical access device can include an elongate member comprising an expansion lumen between a proximal end and a distal end, and an expandable body operably attached to the distal end of the elongate member. The expandable body can be inserted to an internal location in a body in a collapsed configuration. When in a desired position, the expandable body can be expanded outward to an expanded configuration. In the expanded configuration, the expandable body can be adapted to protect adjacent anatomical structures and can have an internal diameter defining an operating lumen sufficient to allow passage of a cannula through the operating lumen. The expandable body may be further expanded inward to a constricting configuration whereby the expandable body can be adapted to constrict about and anchor the cannula in the operating lumen.

8 Claims, 5 Drawing Sheets

EXPANDABLE SURGICAL ACCESS DEVICE AND METHODS OF USE

FIELD OF THE INVENTION

The following description relates to an expandable surgical access device, systems and kits comprising an expandable surgical access device, and methods for using an expandable surgical access device.

BACKGROUND

Conventional surgical procedures for pathologies and/or trauma located deep within the body can cause significant trauma to intervening tissues. Open surgical procedures often require a long incision, extensive muscle stripping, prolonged retraction of tissues, denervation, and devascularization of tissue in order to access a surgical site. Most of these surgeries require several hours of recovery room time and several weeks of post-operative recovery time due to the use of general anesthesia and damage to tissue during the surgical procedure. In some cases, these invasive procedures can lead to permanent scarring and pain.

For example, a common open procedure for disc herniation, laminectomy followed by discectomy, requires stripping or dissection of the major muscles of the back to expose the spine. In an open posterior approach, tissue including spinal nerves and blood vessels around the dural sac, ligaments, and muscle must be retracted to clear a pathway from the skin to the disc. These procedures normally take at least one to two hours to perform under general anesthesia and require post-operative recovery periods of at least several weeks. In addition to the long recovery time, damage to tissue is a major disadvantage of open spinal procedures. As a result, many patients may be reluctant to seek surgery as a solution to pain caused by spinal conditions.

Minimally invasive alternatives, such as endoscopic techniques, reduce pain, post-operative recovery time, and damage to healthy tissue. In minimally invasive surgery, the site of pathology is accessed through portals or a small incision rather than through a significant incision, thus preserving the integrity of intervening tissues. These minimally invasive techniques also often require only local anesthesia. The avoidance of general anesthesia can reduce post-operative recovery time and the risk of complications.

Minimally invasive surgical techniques are particularly desirable for spinal and neurosurgical applications because of the need for access to locations deep within the body and the danger of damage to vital intervening tissues. For example, such minimally invasive techniques can be utilized for spinal discectomy, or removal of an intervertebral disc, and spinal fusion, in which two or more vertebrae are fused together to stop the motion between them. In such minimally invasive, or micro-surgical, procedures, the disc can be accessed by creating a pathway from the surface of the patient's back to the disc through a percutaneous portal or small incision. Such endoscopic surgical techniques typically utilize a tubular structure known as a cannula which is inserted into the percutaneous portal or small incision to a location in the body. The cannula holds the portal or incision open and serves as a conduit extending between the exterior of the body and the local area inside the body where the surgery is to be performed. Small diameter micro-surgical instruments may be passed through the cannula and, for example, into the disc. The intervening tissues are disrupted less because the incision and the exterior-to-interior pathway are smaller.

Although these micro-surgical procedures are less invasive, they can still involve some of the same risk of complications associated with open procedures. For example, the relatively small size of the passage into the body defined by an access cannula adjacent vital anatomical structures can allow injury to those structures, such as the nerve root and dural sac.

Thus, it may be desirable to provide a device capable of protecting anatomical structures along a surgical access pathway in a minimally invasive surgical procedure.

SUMMARY

Described herein are embodiments of an expandable surgical access device and/or system, kits comprising an expandable surgical access device, and/or methods for using an expandable surgical access device. In an illustrative embodiment, an expandable surgical access device can include an elongate member comprising an expansion lumen between a proximal end and a distal end, and an expandable body operably attached to the distal end of the elongate member. The expandable body can be percutaneously inserted to an internal location in a body in a collapsed configuration. When in a desired position at the internal location, the expandable body can be expanded outward to an expanded configuration. In the expanded configuration, the expandable body can be adapted to protect adjacent anatomical structures and can have an internal diameter defining an operating lumen sufficient to allow passage of a cannula, such as a surgical access cannula, through the operating lumen. In some embodiments, the expandable body may be further expanded inward to a constricting configuration whereby the expandable body can be adapted to constrict about and anchor the cannula in the operating lumen.

In certain embodiments, the expandable body can further comprise two expandable bodies. In such embodiments, a first expandable body can be expanded outward to the expanded configuration to protect adjacent anatomical structures and to have an operating lumen for passage of a cannula. A second expandable body in axial alignment with the first expandable body can be expanded inward to a constricting configuration to constrict about and anchor the cannula in the operating lumen.

Some embodiments can include a system and/or kit. Such a system and/or kit can include an expandable surgical access device as described herein. The system and/or kit may further comprise additional components, for example, a surgical access cannula and/or surgical instruments.

Some embodiments can include a method of using an expandable surgical access device to create a surgical access. Such a method can include providing an elongate member comprising an expansion lumen between a proximal end and a distal end and an expandable body operably attached to the distal end of the elongate member; percutaneously inserting the expandable body to an internal location in a collapsed configuration; expanding the expandable body outward to an expanded configuration adapted to protect adjacent anatomical structures and having an internal diameter defining an operating lumen; and inserting a cannula through the operating lumen. Such an embodiment can further include expanding the expandable body inward to a constricting configuration adapted to constrict about and anchor the cannula in the operating lumen.

Features of an expandable surgical access device, system, kit, and/or method may be accomplished singularly, or in combination, in one or more of the embodiments. As will be realized by those of skill in the art, many different embodiments of an expandable surgical access device, system, kit, and/or method are possible. Additional uses, advantages, and features of such embodiments are set forth in the illustrative embodiments discussed in the detailed description herein and will become more apparent to those skilled in the art upon examination of the following.

DETAILED DESCRIPTION

Figure 1:
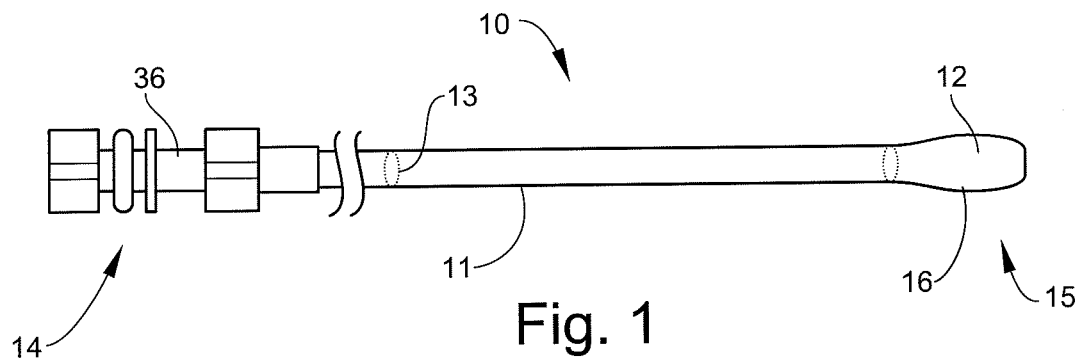
FIG. 1 is a view of an embodiment of an expandable surgical access device showing an expandable body in a collapsed configuration.

For the purposes of this specification, unless otherwise indicated, all numbers expressing quantities, conditions, and so forth used in the specification are to be understood as being modified in all instances by the term "about." Accordingly, unless indicated to the contrary, the numerical parameters set forth in the following specification are approximations that can vary depending upon the desired properties sought to be obtained by the embodiments described herein. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the described embodiments are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, for example, 5.5 to 10. Additionally, any reference referred to as being "incorporated herein" is to be understood as being incorporated in its entirety.

As used in this specification and the appended claims, the singular forms "a," "an," and "the" include plural referents unless the context clearly dictates otherwise. Thus, for example, the term "an expandable body" is intended to mean a single expandable body or more than one expandable body. As used in this specification and the appended claims, "proximal" is defined as nearer to a point of reference such as an origin, a point of attachment, or the midline of the body. As used in this specification and the appended claims, "distal" is defined as farther from a point of reference, such as an origin, a point of attachment, or the midline of the body. Thus, the words "proximal" and "distal" refer to direction nearer to and farther from, respectively, an operator (for example, surgeon, physician, nurse, technician, etc.) who inserts a medical device into a patient, with the tip-end (i.e., distal end) of the device inserted inside the patient's body. For example, the end of a medical device inserted inside the patient's body is the distal end of the medical device, while the end of the medical device outside the patient's body is the proximal end of the medical device.

This description includes embodiments of an expandable surgical access device, systems and/or kits comprising an expandable surgical access device, and methods of using an expandable surgical access device. Embodiments may be useful for creating a surgical access pathway for performing minimally invasive surgery or for accessing an internal organ or tissue.

Figure 2:
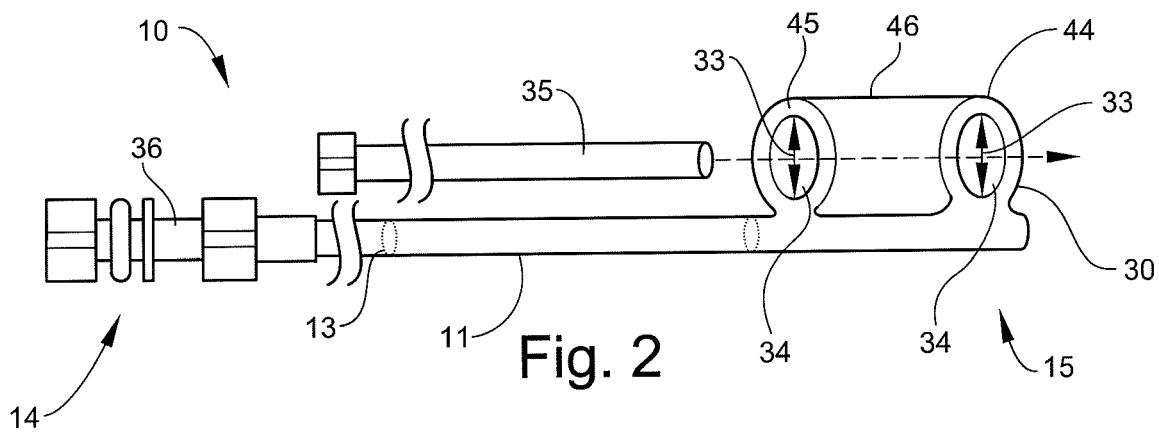
FIG. 2 is a view of an embodiment of an expandable surgical access device having two expandable bodies in an expanded configuration.

In an illustrative embodiment, as shown in FIGS. 1 and 2, an expandable surgical access device 10 can comprise an elongate member 11 and an expandable body 12. The elongate member 11, such as a cannula or catheter, can include an expansion lumen 13 between a proximal end 14 and a distal end 15. The expandable body 12, for example, a balloon, can be operably attached to the distal end 15 of the elongate member 11. The expandable body 12 can be percutaneously inserted to an internal location in a patient's body in a collapsed configuration 16, as shown in FIG. 1. For example, the expandable body 12 can be percutaneously inserted to a surgical site, such as the posterolateral aspect of an intervertebral disc 20 between two nerves in "Kambin's triangle 21."

"Kambin's triangle 21," or "Kambin's access," (shown in FIGS. 3-4 and described below) is a site of surgical, diagnostic, and/or therapeutic access for intervertebral discs. It is defined as a right triangle over a dorsolateral disc. The hypotenuse of the triangle is the exiting nerve 22, the base (width) is the superior border 23 of the caudal, or inferior, vertebra 26, and the height is the traversing nerve root 24. Staying within the confines of this triangular zone allows a surgeon to access the disc without removing bone, while protecting the spinal canal and nearby nerves.

When the expandable body 12 on or near the distal end 15 of the elongate member 11 is placed in a desired location, the proximal end 14 of the elongate member 11 can extend through the patient's skin to a location external to the patient. When in the desired location, the expandable body 12 can be expanded, or inflated, outward to an expanded configuration 30, as shown in FIG. 2. For purposes herein, "expandable" is defined as the ability of the expandable body 12 to be changed from a relatively smaller configuration to a relatively larger configuration. For example, the expandable body 12 can be changed from the collapsed configuration 16 to the expanded configuration 30. In embodiments, the entire expandable body 12 can expand. That is, the expandable body 12 may expand along its entire length 55, and/or through the entire thickness of the body 12 from the inwardly facing wall 42 to the outwardly facing wall 43.

The expandable body 12 and the expanded configuration 30 can comprise various shapes or configurations. For example, the expanded configuration 30 can comprise a doughnut-shaped configuration, that is, a cylindrical shape or configuration 31 having a central aperture. In embodiments of the expandable body 12 having the cylindrical configuration 31, the expandable body 12 can expand outwardly in a substantially radial fashion. In other embodiments, the expandable body 12 and the expanded configuration 30 can comprise a non-circular configuration. For example, the expandable body 12, and the expanded configuration 30, may comprise a profile having a triangular, rectangular, square, or other shape.

In the expanded configuration 30, the expandable body 12 can be configured to protect adjacent anatomical structures, for example, nerves adjacent the intervertebral disc 20. In some embodiments, the expandable body 12 can distract anatomical structures out of an access pathway and provide protection against potential undesired manipulation of those structures by other instruments. In other embodiments, the expandable body 12 can protect anatomical structures, such as nerves, by shielding those structures from other instruments without distracting the structures from their original locations. Outward, or lateral, displacement of a nerve avoids the risk of the nerve being pinched, nicked, or otherwise undesirably moved along the length of the surgical access path by, for example, axial insertion of a surgical access device or other surgical instruments.

The expandable body 12 can be inserted to a desired location in a patient in the collapsed configuration 16, comprising a folded, or wrapped, state. As a result, the expandable body 12 can have a very low, or condensed, profile, for example, 1-2 mm in diameter. Thus, in certain embodiments, the elongate member 11 and attached expandable body 12 can have a smaller external diameter 32 than conventional surgical access cannulae through which surgical instruments can be inserted to a surgical site. Accordingly, the expandable surgical access device 10 can be utilized to reach within closely positioned anatomical structures to protect those structures by shielding and/or distraction.

In addition, in the expanded configuration 30, the expandable body 12 can have an internal diameter 33 that defines an operating lumen 34 sufficient to allow passage of a cannula 35 and/or other surgical instruments through the lumen 34. The expanded, cylindrically-shaped expandable body 12, or balloon, can have an internal diameter 33 large enough for the surgical access cannula 35 to be inserted through the internal diameter 33 of the expandable body 12 into a surgical site.

The expandable body 12 can be operably connected to, or near, the distal end 15 of the elongate member 11, which can be a cannula or catheter tube. The elongate member 11 can include the expansion lumen 13 along the length of the elongate member 11. The expansion lumen 13 can be connected at the distal end 15 to the expandable body 12 and at the proximal end 14 to a source of expansion material, such as fluid or gas, via an expansion port. The expansion lumen 13 and expandable body 12 can be connected in a closed manner. When the expandable body 12 is a desired location for expanding, the elongate member 11 can extend percutaneously such that the proximal end 14 of the elongate member 11 and the expansion lumen 13 extend to the exterior of a patient's body. An expansion material, such as a fluid or gas, can be injected through a proximal expansion port 36, or injection port, connected to the proximal end 14 of the expansion lumen 13. The expansion lumen 13 can convey the expansion material into the expandable body 12 to cause it to expand. Expansion of the expandable body 12 into the expanded configuration 30 can exert pressure directly against anatomical structures adjacent the expandable body 12, thereby moving those structures out of an access path for surgical instruments to be inserted through the operating lumen 34 of the expandable body 12 to a surgical site.

In some embodiments, the expandable surgical access device 10 can include a cannula anchoring mechanism. The cannula anchoring mechanism can comprise further expansion of the expandable body 12 inward to a constricting configuration 37 adapted to constrict about and anchor the cannula 35 in the operating lumen 34. In such embodiments, the expandable body 12 can be configured to have two expansion endpoints. The first expansion endpoint can occur when the expandable body 12 is expanded outward to the expanded configuration 30 such that the external diameter 32 of the body 12 is large enough to protect the desired adjacent anatomical structures by shielding and/or distracting those structures. At this first expansion endpoint, the internal diameter 33 of the expandable body 12 can be large enough to allow the surgical access cannula 35 to slide through operating lumen 34. The second expansion endpoint can occur when the expandable body 12 is expanded inward to the constricting configuration 37 such that the internal diameter 33 of the expandable body 12 can constrict about and anchor the cannula 35 in the operating lumen 34.

Figure 6:
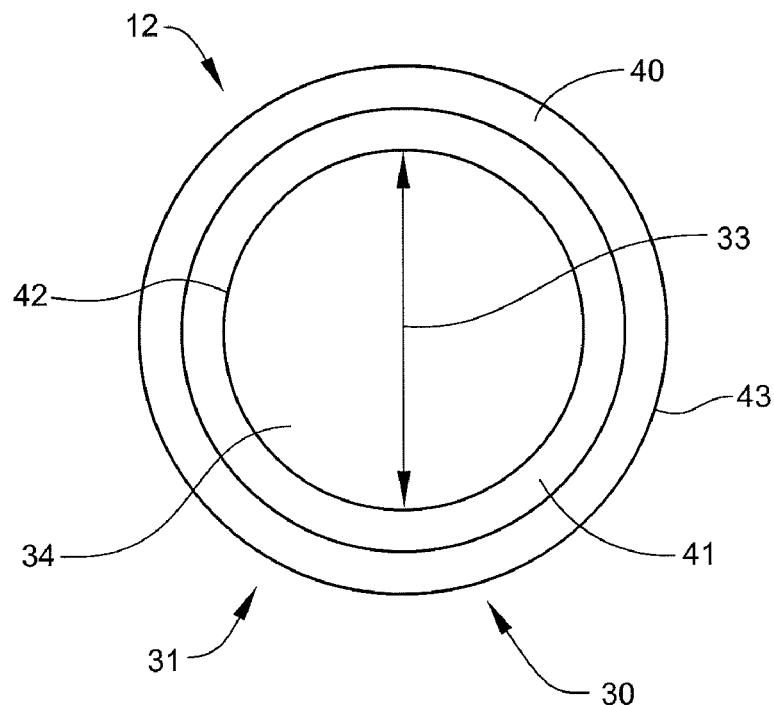
FIG. 6 is a cross-sectional view of an embodiment of an expandable surgical access device in an expanded configuration illustrating an outer expandable portion and an inner expandable portion.
Figure 7:
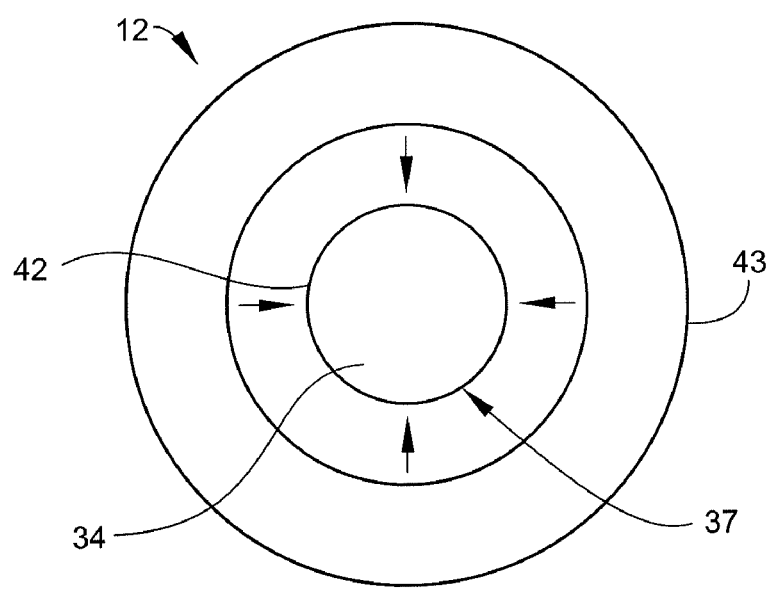
FIG. 7 is a cross-sectional view of an embodiment of an expandable surgical access device illustrating a constricting configuration.

The two expansion endpoints (outward expansion and inward expansion) can be achieved in different ways in various embodiments. For example, as shown in FIGS. 6 and 7, the expandable body 12 can further include two separate expandable portions, an outward expandable portion 40 expandable outwardly and an inward expandable portion 41 expandable inwardly. The elongate member 11 can include two separate expansion lumens 13, one expansion lumen 13 connected to the outward expandable portion 40 and the other expansion lumen 13 connected to the inward expandable portion 41. In this way, the expandable body 12 can be selectively expanded outwardly and inwardly by injecting an expansion material into the expansion lumen 13 connected to the respective expandable portion 40, 41.

In certain embodiments, the inward expandable portion 41 can expand inwardly such that the internal diameter 33 in the constricting configuration 37 can be substantially concentric with the external diameter 32 in the expanded configuration 30. In such an embodiment, the inward expandable portion 41 can constrict in a substantially uniform manner about the cannula 35 (as shown in FIG. 7) and anchor the cannula 35 in the operating lumen 34. In other embodiments, the inward expandable portion 41 can expand inwardly in a non-uniform manner. The inward expandable portion 41 may be configured to expand inwardly such that the inwardly facing wall 42 expands across the majority of the operating lumen 34 to constrict and anchor the cannula 35 generally on a side of the operating lumen 34 where the cannula 35 is placed. For example, the cannula 35 can be placed adjacent a portion of the inwardly facing wall 42 that is somewhat resistant to expansion. A portion of the inwardly facing wall 42 can be made more resistant to expansion than the remainder of the inwardly facing wall 42, for example, by using higher durometer material in the expansion-resistant portion. As a result, when the inward expandable portion 41 is expanded inwardly, the more easily expandable portion of the inwardly facing wall 42 expands across the operating lumen 34 to constrict about and anchor the cannula 35 on one side of the operating lumen 34. In some embodiments, the inner facing wall 42 of the inward expandable portion 41 can expand inwardly to constrict about the entire outside diameter of the cannula 35. In other embodiments, the inner facing wall 42 of the inward expandable portion 41 can expand inwardly to constrict about only a portion of the cannula 35.

In another embodiment, the inwardly facing wall 42 of the expandable body 12 can comprise a stiffer, or higher durometer, material than in the outwardly facing wall 43 of the expandable body 12. In this way, injecting an expansion material into the expansion lumen 13 can initially expand the outwardly facing wall 43 and thus the outer portion of the expandable body 12 to the expanded configuration 30. When an additional amount of expansion material, and/or a greater degree of expansion pressure, is applied through the expansion lumen 13, the inwardly facing wall 42 and thus the inward portion of the expandable body 12 can be expanded to the constricting configuration 37. In other embodiments, outward expansion and inward expansion of the expandable body 12 can be achieved in other manners.

In some embodiments, the expandable body 12 can comprise compliant materials, for example, elastic materials, such that the expandable body 12 can freely expand with insertion of an expansion material. In other embodiments, the expandable body 12 can comprise materials having low compliance, that is, that stretch to a minimal degree or in a restricted manner. In still other embodiments, the expandable body 12 can comprise metallic and/or metal alloy materials, and the expandable body 12 may be expanded mechanically. In one such embodiment, the expandable body 12 can comprise the metal alloy Nitinol, a shape-memory material that can expand from the collapsed configuration 16 to the expanded configuration 30 when released from pressure holding the expandable body 12 in the collapsed configuration 16. Accordingly, some embodiments can include highly elastic, relatively inelastic, and non-elastic materials, each of which may be expanded from the collapsed configuration 16 to the expanded configuration 30.

In other embodiments, the expandable surgical access device 10 can include at least two expandable bodies 12, as shown in the embodiment in FIG. 2. A first expandable body 44 can be expanded outward to the expanded configuration 30 to protect adjacent anatomical structures. A second expandable body 45 can be expanded inward to the constricting configuration 37 adapted to constrict about and anchor the cannula 35 in the operating lumen 34. The first and second expandable bodies 44, 45, respectively, can be in axial alignment with each other such that the operating lumen 34 of each expandable body 44, 45 is aligned so that the surgical access cannula 35 can be inserted through both expandable bodies 44, 45 to a surgical site. In such embodiments, a separate expansion lumen 13 along the length of the elongate member 11 can be operably connected to each of the expandable bodies 44, 45. In other embodiments, each of the first and second expandable bodies 44, 45, respectively, can include both an outer expandable portion 40 for expanding to the expanded configuration 30 and an inner expandable portion 41 for expanding to the constricting configuration 37. As shown in the embodiment in FIG. 2, an expandable body connector 46 can connect the first and second expandable bodies 44, 45, respectively, at a point on the periphery of each of the expandable bodies 44, 45. The expandable body connector 46 can provide some additional stability to the expandable bodies 44, 45 and help to align the expandable bodies 44, 45 when expanded.

Figure 3:
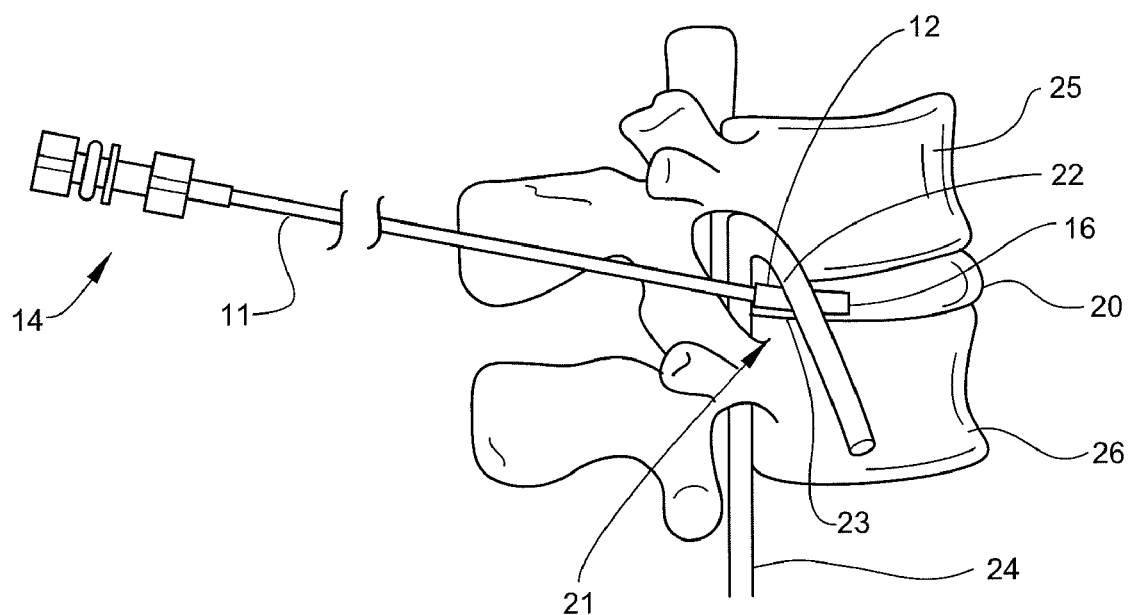
FIG. 3 is an elevation view of an embodiment of an expandable surgical access device with the expandable body in a collapsed configuration within Kambin's triangle adjacent an intervertebral disc.
Figure 4:
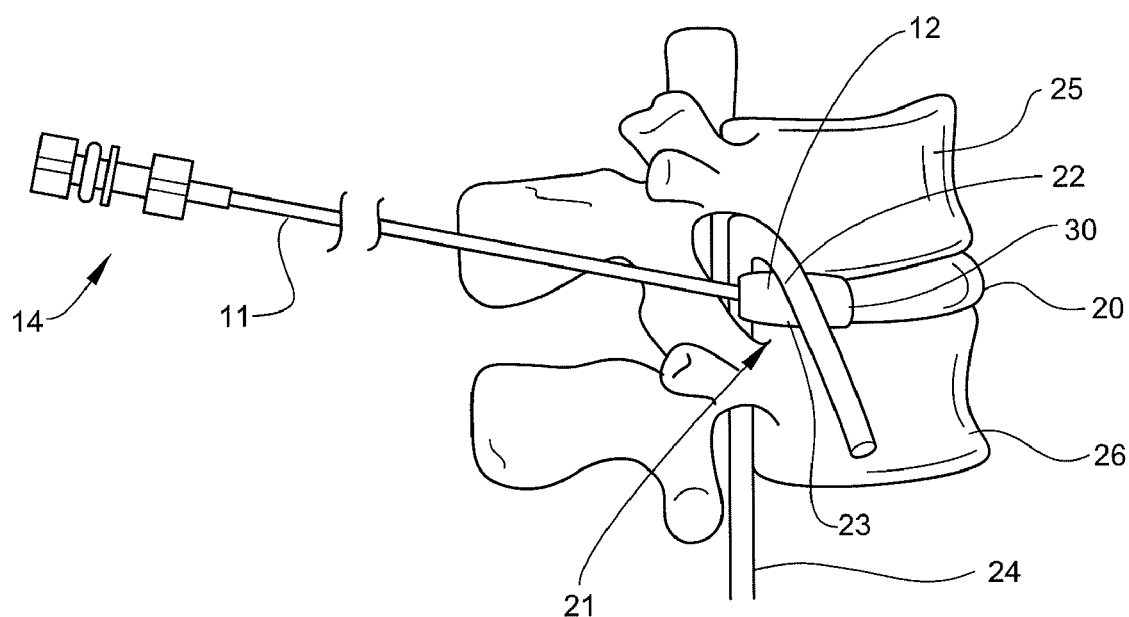
FIG. 4 is an elevation view of the expandable surgical access device shown in FIG. 4, with the expandable body in an expanded configuration within Kambin's triangle adjacent an intervertebral disc.

Referring now to FIGS. 3-4, an elevation (lateral) view of two human vertebrae 25, 26 is shown with an intervertebral disc 20 between the two vertebrae 25, 26. The expandable surgical access device 10 is illustrated establishing a percutaneous path along its elongated axis to a dorsolateral aspect of the disc 20. As shown in FIG. 3, the expandable body 12 can be inserted in the collapsed, or non-expanded, configuration 16 between the traversing nerve root 24, the nerve 22 exiting the spinal canal, and the superior border 23 of the caudal, or inferior, vertebra 26 (that is, within Kambin's triangle 21). Once the expandable body 12 is in the desired position with Kambin's triangle 21, the body 12 can be expanded to the expanded configuration 30, as shown in FIG. 4, to protect the nerves 22, 24, and in particular, the exiting nerve 22 by shielding and/or distracting the nerve 22.

Embodiments of the expandable surgical access device 10 can be placed in a desired anatomical location using various techniques. A desired anatomical location may be in a surgical site, adjacent or near a surgical site, or at a point along a surgical access path distant from a surgical site, depending on the anatomical structure(s) desired to be protected. Delivery of the device 10 to a desired anatomical location can be accomplished utilizing minimally invasive surgical techniques. For example, an initial percutaneous path can be established with a small, conventional insertion needle or cannula (not shown) to penetrate tissue to the surgical site. A stab, or puncture, wound or small incision can be made, through which the insertion cannula can be inserted through the patient's skin to the surgical site. The insertion cannula can comprise, for example, a trocar cannula, a stylet having a sharp tip, and/or a Jamshidi needle. A guide wire (not shown) may be placed through a lumen of the small insertion cannula. The insertion cannula can be removed from the percutaneous path, leaving the guide wire in place. The expandable surgical access device 10 can then be guided over the guide wire so that the expandable body 12 is in a desired position. The guide wire can have a diameter and rigidity sufficient to guide the expandable surgical access device 10 accurately to the surgical site.

In certain surgical applications, access techniques, and/or embodiments of the expandable surgical access device 10, initial access and delivery of the expandable surgical access device 10 can be accomplished in alternative ways. For example, initial percutaneous insertion access and delivery of the expandable surgical access device 10 may be achieved utilizing instruments other than, or in addition to, the small insertion cannula, guide wire, and/or Jamshidi needle. One such device that may be adapted for delivery of the expandable surgical access device 10 that comprises a delivery cannula useful in a minimally invasive technique is described and shown in co-pending U.S. patent application Ser. No. 11/448, 228, which is incorporated herein by reference in its entirety.

Once the expandable body 12 is in a desired position, for example, adjacent the intervertebral disc 20, the expandable body 12 can be expanded. In this way, tissues adjacent the expandable body 12 can be gently and safely shielded and/or distracted to provide a surgical access pathway away from the spinal canal and nerves 22, 24. A larger diameter, surgical access cannula 35 can then be inserted through the operating lumen 34 provided when the expandable body 12 is expanded. As a result, tissue such as nerves 22, 24 that might otherwise be in the path of the surgical access cannula 35 can be safely protected to avoid being inadvertently moved along the surgical access pathway, nicked, or undesirably disturbed as the surgical access cannula 35 is axially inserted to the surgical site.

Minimally invasive spinal procedures with which embodiments of the expandable surgical access device 10 are useful are advantageous in that they can utilize endoscopic equipment for viewing the surgical site. Due to the smaller access portal to the surgical site, miniaturized instruments, such as scrapers and drills, can be used to operate on the intervertebral space. In a minimally invasive procedure, the muscle can be split or moved apart rather than cut, as in an open procedure. As a result, minimally invasive spinal procedures can provide decreased bleeding, less pain, a reduced hospital stay, shorter recuperating time, and less long term tissue damage.

Figure 5:
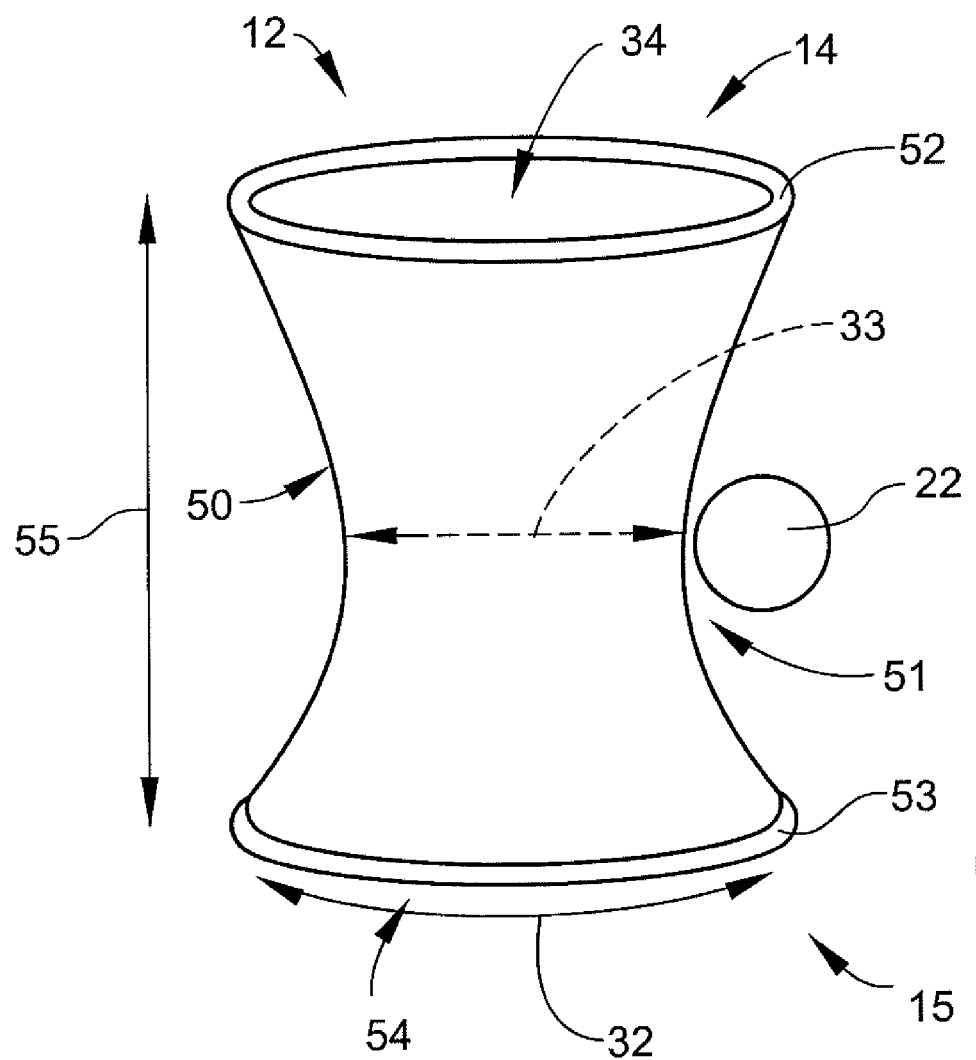
FIG. 5 is a view of another embodiment of an expandable body of an expandable surgical access device.

In certain embodiments, the expandable body 12 can comprise a curvilinear configuration 50, as shown in FIG. 5. In such a curvilinear configuration 50, the proximal and distal ends 14, 15, respectively, of the expandable body 12 can have an external diameter 32 greater than the external diameter 32 of a middle portion 51 along the length 55 of the body 12. In this way, the curved, concave sides of the expandable body 12 in the expanded configuration 30 can extend farther about the adjacent nerves 22, 24 than an expandable body 12 having rectilinear sides or sides that are convex. As a result, the curvilinear expandable body configuration 50 may provide a more protective barrier against inadvertent contact with the nerves 22, 24 with access tools and/or surgical instruments. The expandable body 12 having the curvilinear configuration 50 can be molded into such a shape. As shown in the embodiments in FIGS. 2, 5, 6, and 7, the cross-sections of the proximal and distal ends 14, 15, respectively, of the expandable body 12 can have the same size.

In certain embodiments, the expandable body 12 can include a proximal rim 52 and a distal rim 53, as shown in FIG. 5. The proximal and/or distal rims 52, 53, respectively, can have a greater thickness than the remainder of the expandable body 12. For example, the proximal and/or distal rims 52, 53, respectively, can comprise an additional thickness of the material from which the expandable body 12 is formed. Alternatively, or in addition, the proximal and/or distal rims 52, 53, respectively, can have greater rigidity than the remainder of the expandable body 12. Such greater rigidity may be produced by heating the mold differently or using a different extrusion technique for the rims 52, 53 than in the remainder of the body 12. In certain embodiments, the proximal and/or distal rims 52, 53, respectively, can be reinforced with other material(s) stiffer than the material in the remainder of the expandable body 12. The proximal and distal rims 52, 53, respectively, may each comprise the same materials and be formed in the same manner. Alternatively, the proximal and distal rims 52, 53, respectively, can comprise different materials and/or be formed using different techniques to provide different rigidities. For example, particular embodiments may have the distal rim 53 having a greater rigidity than the proximal rim 52 for the purpose of providing a more substantial contact point for the expandable body 12 to rest against the intervertebral disc 20. In such an embodiment, the more substantial distal rim 53 can comprise a disc contacting surface 54.

Some embodiments of the expandable surgical access device 10 can comprise various other components and configurations.

The expandable body 12 can have various dimensions. For example, in an embodiment in which the expandable body 12 is designed to protect nerves in Kambin's triangle 21, the proximal to distal length 55 of the body 12 can be in the range of about 0.5 to 1.0 cm. An expandable body length 55 in this range is sufficient to protect nerves 22, 24 adjacent the intervertebral disc 20. In other embodiments, the proximal to distal length 55 of the expandable body 12 can be about 3.0 cm or more, for example, as shown in FIG. 3. In certain embodiments of such length 55, the expandable body 12 can extend from a surgical site to the exterior of the patient's body. Such longer embodiments of the expandable body 12 can help stabilize the surgical access pathway along its length.

The internal diameter 33 of the expandable body 12 in its expanded configuration 30 can be sized to provide a sufficient pathway for passage of a particular sized surgical access cannula 35 and/or surgical instruments needed for a particular surgical procedure. The internal diameter 33 of the operating lumen 34 of the expandable body 12 when expanded can be in certain embodiments, for example, about 7 mm. In other embodiments, the internal diameter 33 of the expandable body 12 when expanded can be greater or less than about 7 mm, depending on the size of the surgical access cannula 35 and/or surgical instruments to be inserted through the operating lumen 34 of the expanded body 12 to a surgical site.

The expandable body(ies) 12 of the expandable surgical access device 10 can comprise material(s) that allow expansion with a fluid or gas so as to expand the body(ies) 12 into the expanded configuration 30. Such materials can include, for example, medical grade plastics like vinyl, nylon, polyethylenes, ionomer, polyurethane, and polyethylene tetraphthalate (PET). Such material(s) can be selected to exhibit generally elastic properties, like latex, or less elastic properties, like silicone.

In some embodiments, movement and positioning of the expandable body 12 can be monitored fluoroscopically or under CT visualization. For example, fluid inserted into the expandable body 12 via the expansion lumen 13 of the elongate member 11 can be radiopaque such that expansion of the expandable body 12 can be monitored. Radiopaque is defined as being opaque to radiation and especially x-rays. In alternative embodiments, the wall(s) of the expandable body 12 can be formed from a radiopaque material. In each of embodiments in which the expandable body 12 is expanded with a radiopaque fluid or in which the walls of the expandable body 12 comprise a radiopaque material, the size, shape, and/or movement and positioning of the expandable body 12 can be visualized.

In certain embodiments, a plurality of radiographic markers can be in communication with predetermined portions of the expandable body 12 so that when the expandable body 12 expands, movement and positioning of the markers—and the expandable body 12 in communication therewith—can be visualized. In certain embodiments, radiographic markers can be in communication with the outward expandable portion 40 (as shown in FIG. 6) of the expandable body 12. In this manner, when the expandable body 12 is expanded, the outer perimeter of movement and positioning of the expandable body 12 can be visualized. Accordingly, positioning of the outer expandable portion 40 of the expandable body 12 against adjacent tissue, and movement of that tissue for creating a surgical access path, can be monitored. In other embodiments, radiographic markers can be in communication with the inward expandable portion 41 (as shown in FIG. 6) of the expandable body 12 such that when the expandable body 12 is expanded, the inner perimeter of movement and positioning of the expandable body 12 can be visualized. In still other embodiments, radiographic markers can be in communication with both the outward expandable portion 40 and the inward expandable portion 41 of the expandable body 12 such that both the outer and inner perimeters of movement and positioning of the expandable body 12 can be visualized.

Radiopaque materials useful for inclusion in the walls of the expandable body 12 include, for example, barium sulfate, tantalum, tungsten, and bismuth subcarbonate. A powder of such radiopaque materials can be compounded with selected materials for making the expandable body 12 and extruded together with the selected materials to form a tube.

Certain embodiments of the expandable surgical access device 10 can include an expansion indicator mechanism (not shown) to indicate the degree to which the expandable body 12 is expanded. For example, components of the expandable surgical access device 10, such as the outward expandable portion 40 and the inward expandable portion 41 of the expandable body 12 can include radiopaque indicators for this purpose. In this way, expansion of the expandable body 12 can be visualized under fluoroscopy. Alternatively, or in addition, the expandable body 12 may have a volume expansion, or inflation, indicator (not shown), that can indicate when the expandable body 12 is expanded to a certain predetermined degree, including when the expandable body 12 is fully expanded into the fully expanded configuration 30 and into the constricting configuration 37. Such an expansion indicator mechanism can indicate a degree of expansion of either the outward expandable portion 40 or the inward expandable portion 41, or both.

Embodiments of the expandable surgical access device 10 can have advantages over conventional surgical access devices. For example, one advantage is that the expandable body 12 can be delivered to a desired location in the collapsed configuration 16 and expanded into the expanded configuration 30 when in position in the desired location. As a result, the surgical access device 10 can be delivered to the desired location in a smaller profile than other similar devices. In addition, the expandable body 12 can be expanded outward in order to protect adjacent anatomical structures, such as nerves 22, 24 by shielding and/or distracting the nerves 22, 24. Outward, or lateral, displacement of a nerve avoids the risk of the nerve being pinched, nicked, or otherwise undesirably moved along the length of the surgical access path by axial insertion of surgical instruments. That is, when a conventional surgical access cannula is inserted, the axial motion of such insertion can nick a nerve or other tissue or inadvertently push the nerve or tissue along the surgical access path. Such undesired movement and/or trauma to a nerve or other tissue can be a particular risk when multiple graduated dilators or gradually larger concentric tubes are used to enlarge a surgical access pathway.

Another advantage of embodiments of the expandable surgical access device 10 is that such embodiments can be quicker, easier, and less expensive to use than conventional surgical access devices. For example, use of embodiments of the expandable surgical access device 10 can avoid the additional equipment, time, and cost, of inserting sequentially larger graduated dilators, or gradually larger concentric cannula dilators one over the other, to enlarge a surgical access pathway.

Another advantage of embodiments of the expandable surgical access device 10 is that such embodiments can be utilized in minimally invasive surgical techniques.

This disclosure includes embodiments of an expandable surgical access device system and/or kit. Such a system and/or kit can include embodiments of the expandable surgical access device 10 as described herein. For example, some embodiments of such a system and/or kit can include the expandable surgical access device 10 comprising the elongate member 11 having the expansion lumen 13 between the proximal end 14 and the distal end 15, and the expandable body 12 operably attached to the distal end 15 of the elongate member 11. The expandable body 12 can be percutaneously inserted to an internal location in a body in the collapsed configuration 16. When in a desired position at the internal location, the expandable body 12 can be expanded outward to the expanded configuration 30. In the expanded configuration 30, the expandable body 12 can be adapted to protect adjacent anatomical structures and can have the internal diameter 33 defining the operating lumen 34 sufficient to allow passage of a cannula, such as the surgical access cannula 35, through the operating lumen 34. In some embodiments of a system and/or kit, the expandable body 12 may be further expanded inward to the constricting configuration 37 whereby the expandable body 12 can be adapted to constrict about and anchor the cannula 35 in the operating lumen 34.

In certain embodiments of a system and/or kit, the expandable body 12 can further comprise two expandable bodies 44, 45. In such embodiments, the first expandable body 44 can be expanded outward to the expanded configuration 30 to protect anatomical structures and to have the operating lumen 34 for passage of the cannula 35. The second expandable body 45 in axial alignment with the first expandable body 44 can be expanded inward to the constricting configuration 37 to constrict about and anchor the cannula 35 in the operating lumen 34.

Some embodiments of a system and/or kit can include the expandable body 12 separate from the elongate member 11. In such embodiments, the expandable member 12 can be connected to the elongate member 11 in the operating setting for operation. Alternatively, or in addition, the system and/or kit can include the surgical access cannula 35 along with the expandable body 12 and elongate member 11. In other embodiments, the surgical access device 10 can be packaged with other surgical instruments and tools for performing a particular surgical procedure, for example, a discectomy. In certain embodiments, several expandable bodies 12 having various sizes and/or configurations can be packaged together with the expandable surgical access device 10 so that a surgeon can select the expandable body 12 appropriate for protecting a particular anatomical structure or a particular patient's anatomy.

Figure 8:
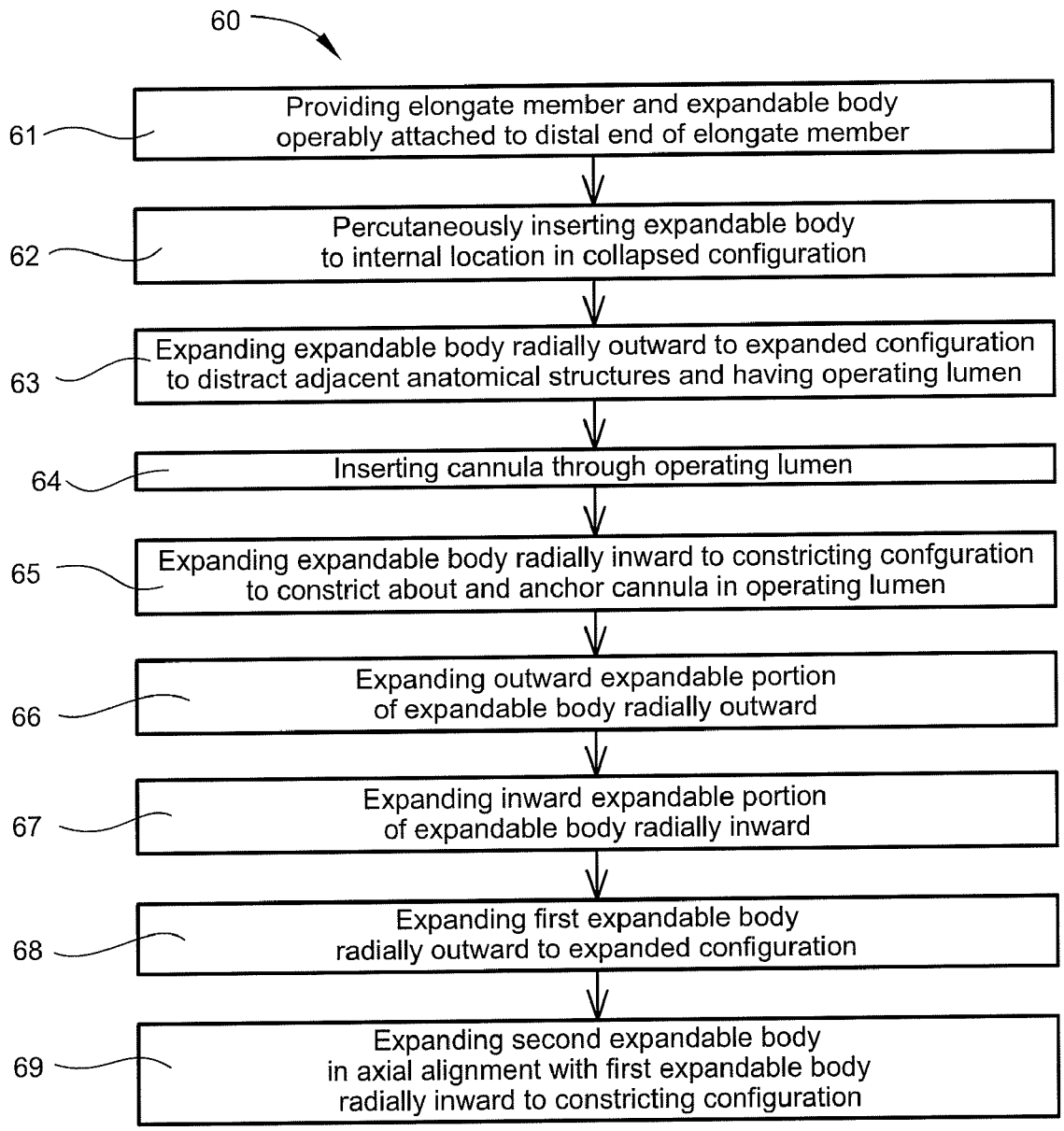
FIG. 8 is a chart illustrating an embodiment of a method of using an expandable surgical access to create a surgical access pathway.

Some embodiments can include a method for using the expandable surgical access device 10, system, and/or kit as described herein, to create a surgical access pathway. As shown in the embodiment illustrated in FIG. 8, one such method 60 can comprise accessing a surgical site utilizing the expandable surgical access device 10. That is, the method 60 can include providing (61) the elongate member 11 comprising the expansion lumen 13 between the proximal end 14 and the distal end 15, and the expandable body 12 operably attached to the distal end 15 of the elongate member 11. The method 60 can further include percutaneously inserting (62) the expandable body 12 to an internal location, such as adjacent the intervertebral disc 20, in the collapsed configuration 16. The method 60 can further include expanding (63) the expandable body 12 outward to the expanded configuration 30 adapted to protect adjacent anatomical structures and having the internal diameter 33 defining the operating lumen 34. In some embodiments, a cannula, such as the surgical access cannula 35, can then be inserted (64) through the operating lumen 35. In certain embodiments, such a method 60 can further include expanding (65) the expandable body 12 inward to the constricting configuration 37 adapted to constrict about and anchor the cannula 35 in the operating lumen 34.

In some embodiments, the expandable body 12 can include the outward expandable portion 40 and the inward expandable portion 41. In such embodiments, expanding (63) the expandable body 12 outward can include expanding (66) the outward expandable portion 40 of the expandable body 12 outward, and expanding (65) the expandable body 12 inward can include expanding (67) the inward expandable portion 41 of the expandable body 12 inward.

In other embodiments, the expandable surgical access device 10 can comprise two expandable bodies 44, 45 positioned such that in the expanded configuration 30, the operating lumen 34 of each expandable body 44, 45 is in axial alignment with that of the other expandable body 44 or 45.

The internal diameter 33 of each operating lumen 34 can be sufficient to allow passage of the surgical access cannula 35 through the two expandable bodies 44, 45. The first expandable body 44 can be expanded (68) outward to the expanded configuration 30 to protect adjacent anatomical structures. The second expandable body 45 can be expanded (69) inward to the constricting configuration 37 to constrict about and anchor the cannula 35 in the operating lumen 34.

In embodiments of a method, the expandable body 12 can comprise various expanded configurations 30. For example, the expanded configuration 30 of the expandable body(ies) 12, 44, 45 can be a cylindrical configuration 31 (as shown in FIGS. 2, 6, and 7). In other embodiments, the expandable body 12, 44, 45 can have the curvilinear configuration 50 (as shown in FIG. 5) such that proximal and distal ends 14, 15, respectively, of the expandable body 12, 44, 45 have the external diameter 32 greater than an external diameter of the middle portion 51 of the body 12.

Some embodiments of a method (60) can further comprise performing spinal surgery through the operating lumen 34 defined by the internal diameter 33 of the expandable body 12 in the expanded configuration 30. For example, such spinal surgery can include discectomy, vertebral fusion, and/or other surgical, diagnostic, and/or therapeutic procedures on the spine.

Embodiments of the expandable surgical access device 10, system, kit, and method as described herein can be utilized for providing safe and effective surgical access to intervertebral spaces. Some embodiments may be applicable for use with various other types of anatomical structures, for example, joints (ankle, interdigital, etc.) and in various anatomical locations (for example, spine, knees, arms, legs, etc.) of a human or animal body. In the spinal column, embodiments of the surgical access devices and methods may be used at all intervertebral joints, including those in the cervical, thoracic, and lumbar regions. Embodiments of the expandable surgical access device, system, kit, and method as described herein can be utilized in any cannulated surgery, for example, laparoscopic procedures, catheter-facilitated procedures, etc., to safely and gently protect selected anatomical structures and subsequently hold access components in place.

Although this description refers to particular embodiments, it should be recognized that these embodiments are merely illustrative of novel and non-obvious principles. Those of ordinary skill in the art will appreciate that an expandable surgical access device, system, kit, and methods may be constructed and implemented in other ways and embodiments. Accordingly, the description herein should not be read as limiting such embodiments, as other embodiments also fall within the scope of this disclosure.

What is claimed is:

1. A surgical access device for providing surgical access in a patient, comprising:

an elongate member comprising an expansion lumen between a proximal end and a distal end; and a first expandable body operably attached to the distal end of the elongate member, percutaneously insertable through an incision to an internal location in a collapsed configuration, and the first expandable body expandable outward to an expanded configuration configured to exert pressure directly against anatomical structures thereby moving those structures out of an access path for surgical instruments to be inserted through an operating lumen of the first expandable body in the expanded configuration;

a cannula for placement through the first expandable body when the first expandable body is in the expanded configuration;

a second expandable body in axial alignment with the first expandable body operably attached to the distal end of the elongate member, percutaneously insertable through an incision to an internal location in a collapsed configuration;

expandable inward to a constricting configuration to constrict about and anchor the cannula; and wherein the elongate member is configured to extend through the incision to a location external to the patient when the second expandable body is inserted to the internal location.

2. The device of claim 1, wherein the expanded configuration comprises a cylindrical configuration.

3. The device of claim 1, wherein the first expandable body further comprises a curvilinear configuration such that proximal and distal ends of the first expandable body have an external diameter greater than an external diameter of a middle portion of the body.

4. The device of claim 1, wherein the first expandable body further comprises at least one of a proximal rim and a distal rim, each rim comprising a greater rigidity than a remainder of the first expandable body.

5. The device of claim 1, wherein the internal location is adjacent an intervertebral disc.

6. A surgical access system comprising the surgical access device of claim 1, wherein the first and second expandable body is separate from and connectable with the elongate member.

7. The surgical access device of claim 1, wherein when the first expandable body is in the expanded configuration, the first expandable body has an internal diameter defining the operating lumen sufficient to allow passage of the cannula therethrough.

8. The device of claim 7, wherein the cannula comprises a surgical access cannula.

* * * * *